United States Patent
Dalton

(10) Patent No.: US 7,699,851 B2
(45) Date of Patent: Apr. 20, 2010

(54) BONE CUTTING JIG SYSTEM FOR SPINAL IMPLANT

(76) Inventor: Brian E. Dalton, 333 State St., Erie, PA (US) 16507

( * ) Notice: Subject to any disclaimer, the term of this patent is extended or adjusted under 35 U.S.C. 154(b) by 1388 days.

(21) Appl. No.: 10/445,567

(22) Filed: May 28, 2003

(65) Prior Publication Data

US 2004/0034361 A1  Feb. 19, 2004

Related U.S. Application Data

(63) Continuation-in-part of application No. 10/223,230, filed on Aug. 19, 2002, now abandoned.

(51) Int. Cl.
*A61F 5/00* (2006.01)
(52) U.S. Cl. ...................................................... 606/87
(58) Field of Classification Search ................... 606/53, 606/79, 82, 86–87, 96–98, 102, 86 R
See application file for complete search history.

(56) References Cited

U.S. PATENT DOCUMENTS

| | | | | |
|---|---|---|---|---|
| 4,907,577 A | * | 3/1990 | Wu ............................. | 606/87 |
| 5,275,603 A | * | 1/1994 | Ferrante et al. ............... | 606/86 |
| 5,364,401 A | * | 11/1994 | Ferrante et al. ............... | 606/84 |
| 5,364,402 A | * | 11/1994 | Mumme et al. ............... | 606/88 |
| 5,423,827 A | * | 6/1995 | Mumme et al. ............... | 606/96 |
| 5,601,563 A | * | 2/1997 | Burke et al. ................... | 606/86 |
| 5,653,714 A | * | 8/1997 | Dietz et al. .................... | 606/87 |
| 5,683,396 A | * | 11/1997 | Tokish et al. .................. | 606/87 |
| 5,810,827 A | * | 9/1998 | Haines et al. .................. | 606/80 |
| 5,853,415 A | * | 12/1998 | Bertin et al. .................. | 606/80 |
| 5,916,220 A | * | 6/1999 | Masini ......................... | 606/88 |
| 6,007,537 A | * | 12/1999 | Burkinshaw et al. .......... | 606/66 |
| 6,068,633 A | * | 5/2000 | Masini ......................... | 606/86 |
| 6,159,217 A | * | 12/2000 | Robie et al. ................... | 606/88 |
| 6,258,096 B1 | * | 7/2001 | Seki ............................. | 606/88 |
| 6,500,179 B1 | * | 12/2002 | Masini ......................... | 606/88 |
| 6,648,894 B2 | * | 11/2003 | Abdelgany et al. ............ | 606/79 |
| 6,676,662 B1 | * | 1/2004 | Bagga et al. ................... | 606/87 |
| 2002/0082604 A1 | * | 6/2002 | Abdelgany et al. ............ | 606/79 |

* cited by examiner

*Primary Examiner*—Thomas C Barrett
*Assistant Examiner*—James L. Swiger
(74) *Attorney, Agent, or Firm*—Carothers & Carothers

(57) ABSTRACT

A bone cutting jig system for forming and shaping spinal implants is shown. The system includes a first cutting jig having a bed with a clamp mechanism for clamping donor bone positioned on the bed. A cutting guide insert or plate is received in fixed orientation on the bed and is further provided with two spaced cutting blade cutting guides which are configured for transversely cutting out a segment of the donor bone with a reciprocating saw or router to a predetermined shape to provide a custom fit lumbar, cervical or thoracic inter-body fusion implant. A second cutting jig is provided for making additional cuts to the preformed implant for custom fit to particular implant applications.

8 Claims, 7 Drawing Sheets

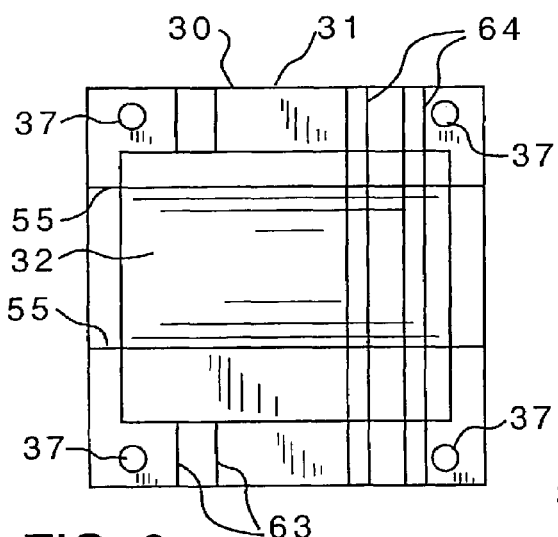
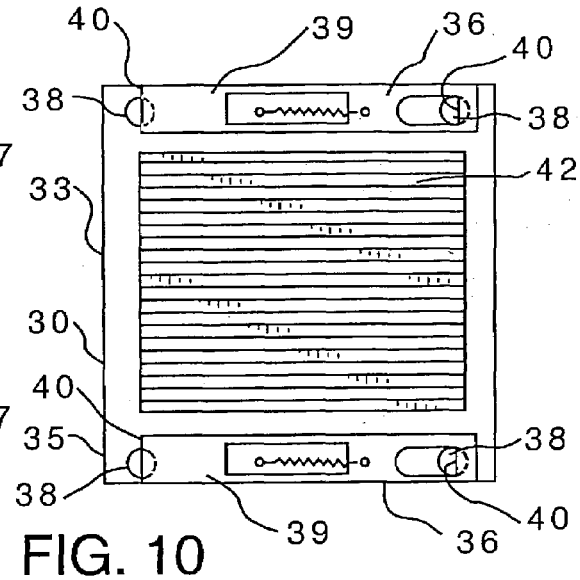
FIG. 9  FIG. 10
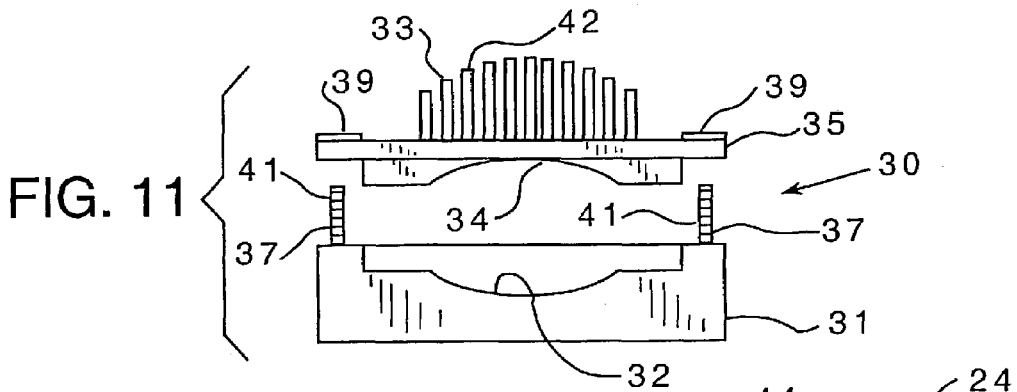
FIG. 11
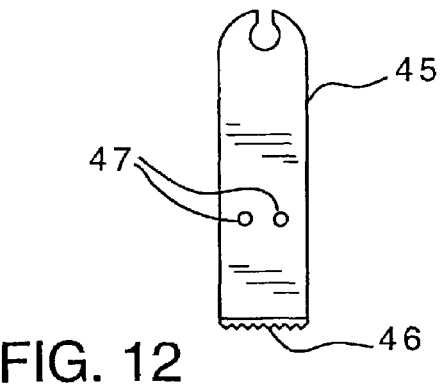
FIG. 12
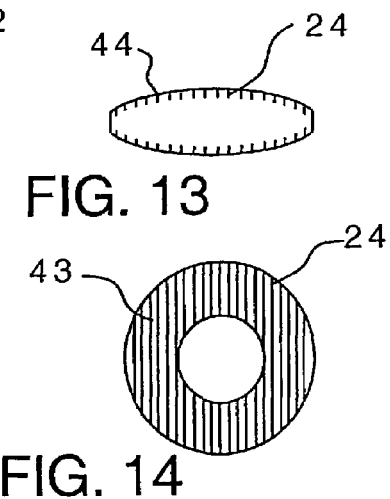
FIG. 13
FIG. 14

BONE CUTTING JIG SYSTEM FOR SPINAL IMPLANT

CROSS REFERENCE

This application is a continuation-in-part of application Ser. No. 10/223,230, filed Aug. 19,2002 now abandoned, for BONE CUTTING JIG SYSTEM FOR SPINAL IMPLANT.

BACKGROUND OF THE INVENTION

1. Field of the Invention

The invention relates to an instrument for cutting and otherwise shaping donor bone for custom fit as spacer implants for spinal fusions in the human spine as a replacement for one or more intervertebral discs in the cervical, thoracic or lumbar spines.

2. Discussion of the Prior Art

When intervertebral discs in the lumbar of humans become injured, degenerated, or diseased, a preferred treatment is to remove the damaged disc and implant in its place a spacer customly constructed from donor bone to facilitate bony fusion by bone growth between adjacent vertebra. Typically the damaged intervertebral disc is removed and bone graft material is packed in the intervertebral space. Such spinal fusions are becoming evermore commonly preformed and the trend is for the procedure to become more complicated involving more and more instrumentation and implants of various sorts and sizes to aide in the fusion construct. Spacer implants are pre-manufactured from donor bone and come in an extremely large variety of shapes and sizes and they are designed according to the vendor's philosophy, not the doctor's philosophy, regarding how the particular implant aides in the construct and fusion process. In addition, these pre-manufactured implants are becoming extremely expensive.

These pre-machined spacer implants are machined by the surgical supply vendors to exact dimensions and packaged according to size of the implant. At the time of surgery, the physician determines the size of the implant required to adequately fill the space to be fused, and a pair of appropriately sized implants are selected and opened. As a present day example, a one level lumbar fusion, utilizing posterior lumbar inter-body fusion implants (PLIF) costs approximately $4,000.00 U.S. Dollars for the PLIF implants alone. For each additional level which is fused, this cost is multiplied. For example a two level fusion implant costs $8,000.00. Over the last decade, greater financial restraints have been placed on hospitals, and subsequently on physicians performing these procedures and surgical implant vendors for lower cost options. Presently no such options are available. In addition, the surgeon has no input or choice in selecting the particular design of the spacer implant to provide a good custom fit.

Recently there has also been pressure to produce biologically conductive PLIF bony implants since the body will eventually assimilate the PLIF material and the PLIF implant does not interfere with follow-up radiographs as do metal implants. The implants need to be formed with exact precision and be exactly reproducible so that there will exist a well formed pair of PLIF implants. It is therefore an object of the present invention to permit the surgeon, himself or herself, to fabricate such donor bone implants quickly within the operating room to exact custom dimensions while the operative case is ongoing.

SUMMARY OF THE INVENTION

The system of the present invention achieves this object and permits the surgeon to custom cut and form the implant from an available bank stock of frozen donor bone. This donor bone also allows multiple implants to be formed or shaped at one operative sitting so that a one level fusion with two PLIF implants would cost the same as a four level fusion requiring eight PLIF implants, since they would all be cut from the same piece of donor bone. The system of the present invention additionally applies to implants for cervical and thoracic modification.

The cutting jig system of the present invention will be available to the surgeon during ongoing surgery and the system serves as a guide for cutting spinal spacer implants from donor bone for spinal fusions. The system in its broadest configuration comprises a first jig having a bed with a clamp mechanism for clamping donor bone positioned on the bed for cutting. A removable cutting guide insert is received in fixed orientation on the bed and has two spaced saw blade or router blade cutting guides configured for transversely cutting out a segment of the donor bone which is clamped on the bed to a predetermined shape and dimension to provide a custom fit lumbar inter-body fusion implant. The spaced cutting blade cutting guides are open-ended guides, typically constructed of metal, and dimensioned to received and guide a reciprocated saw blade or a rotating router blade for cutting through the donor bone along a predetermined profile which is preset by the guide. Thus, a readily available surgical reciprocating saw or router can be employed and typically the implant would be cut from a femur shaft or fibula shaft, a source of bone that is readily available and relatively inexpensive. This allows very fast cutting without binding.

The spaced cutting blade cutting guides are open-ended and dimensioned to receive and guide the reciprocating saw blade or router blade for cutting through donor bone clamped on the bed along a predetermined profile. The spaced cutting guides are typically comprised of open-ended slots of predetermined profile. The space cutting guides are configured for cutting a lens shaped bi-convex cross sectional segment from the donor bone in the instance of a lumbar implant. The space cutting guides are configured for cutting a wedge shaped cross sectional segment from the donor bone for use as cervical or thoracic implants.

Many multiples of the cutting guide inserts are provided whereby each insert has different saw guide profiles from another insert for providing many multiple choices to the physician for dimension and shape for custom fit donor bone implant segments. Normally these cutting guide inserts will be provided in spaced upper and lower matched pairs having identical cutting guide profiles for respectively guiding upper and lower portions of the reciprocating saw blade or router blade. In order to more effectively position and clamp the femur or fibula donor bone onto the bed, the bed is provided with a trough for receiving the elongate donor bone segment therein for clamping.

Accordingly, precision is afforded by the saw guide inserts, which are available in various sizes (implant height) according to the patient's needs. As explained for lumbar application, femur is cut in a lens shape (bi-convex) to allow intimate fit within the disc space, since the disc space has a bi-concave shape. The blade cutting guide inserts provide a bi-convex lens shape which has an overall 11° taper, which enhances the implants capability to impart a lordosis to the fused lumbar segment. This shape resembles the shape of the average lumbar disc space. The PLIF insert may be typically designed to be approximately 22 mm long, which fits well in the average sized lumbar disc space. This length can easily be made longer or shorter according to the wishes of the surgeon due to the flexibility of the system of the present invention.

Once the femoral shaft has been cut with the first cutting jig, the resultant femoral bi-onvex ring is placed into a second jig of the present invention having a bed with a trough therein which is contoured and dimensioned to receive and seat bottom portions of the implant. A cover plate dimensioned and contoured to engage upper portions of this implant is provided and has a clamping mechanism for drawing the cover plate to the bed of this second jig in alignment for properly clamping the implant therebetween. Parallel cutting blade guide slots are provided in this cover for guiding an oscillating cutting blade or a router-type cutting blade to correspondingly cut the implant for either cutting slots to provide ridges thereon or for cutting off segments of the implant. This second cutting jig allows the remainder of the precision cuts to be carried out quickly and easily, while providing the surgeon with dimensional options. The contours of this second jig allow proper seating of the bone insert to assure precision cuts and prevents the bone from moving about during the cutting procedure. Cutting profile reference line indicia or witness marks are provided on the bed for this second jig to provide suggested cutting profiles and proper alignment of the cover plate.

A series of additional cover plates are provided for the bed of this second jig for providing many different cuts. Some of these cover plates may include a mechanism for adjusting spacing between or placement of selected of the slots provided in the cover plate to permit adjustment. The cover plates thus allow significant surgeon driven modification to be performed in the operating room, depending upon the surgeon's judgement regarding the patient's requirements. This flexibility and availability is simply not available with any prior art system.

Lastly, the system of the present invention further includes yet another jig or apparatus for retaining the implant cut out from donor bone on the first and/or second jig and this third jig includes a drill guide for guiding a drill to cut a notch along one side of the implant. This notch is provided for mating engagement with a finger jaw of an insertion clamp for gripping and controlling the implant during lumbar insertion. The insertion clamp is thus provided with a pair of parallel finger jaws for releaseably clamping opposite sides of the implant with one of the finger jaws seated in this afore-described notch.

Not only can the resultant custom spacer implant be variable by size, but it also may be variable in size to application. By using the system of the present invention, the resultant implant can be formed as an ALIF (anterior lumbar inter-body fusion) ring, complete with lordotic curve to aide in precise fit and ridges to help avoid post surgical back out of the implant. Depending upon how the implant is cut on the second jig with the selected cover plate, a TLIF (transforamenal or lateral lumbar inter-body fusion implant) is formed, or if multiple cuts are made on the second jig, a PLIF implant pair may be formed. Again, no system of the prior art allows such flexibility and choice in implant style, size and application.

The bone cutting jig system of the present invention is not only applicable to the cutting and production of a spinal implant for the lumbar area, but also for the manufacture of implants for the cervical and thoracic areas of the spine. For these latter applications, a first cutting jig is employed for cutting a segment of femur or fibula donor bone to a wedge shape of three degrees. This bone segment is then moved to a second cutting jig for cutting other required contours and dimensions to the implant. All of these initial cuts and subsequent cuts are made with a cutting jig similar to that already described for cutting final dimensions and contours to a lumbar implant.

This cutting jig system includes a cutting jig having a bed contoured in dimension to receive and seat bottom portions of an implant cut from donor bone. A cover plate that is dimensioned and contoured to engage upper portions of the implant is provided with a clamp mechanism for drawing the cover plate to the underlying bed in alignment for clamping the implant therebetween. Cutting blade guide slots are provided in the cover plate for guiding a cutting blade, such as a reciprocating saw blade or router blade, to corresponding cut the implant.

For initial cuts in cervical and thoracic applications, the cover plate guide slots are comprised of two spaced diverging slots angled at approximately three degrees relative to each other in order to cut off a segment of femur or fibula donor bone. For contouring and dimensioning cuts thereafter, a second jig is used with a selection of cover plates having guide slots which are comprised of parallel slots spaced at predetermined intervals as required to cut and contour the implant.

Surfaces of the jig bed and/or cover plate which will engage the implant when positioned in the jig are preferably roughened for permitting nonslip engagement of the implant.

BRIEF DESCRIPTION OF THE DRAWINGS

Other objects and advantages appear hereinafter in the following description and claims. The accompanying drawings show, for the purpose the exemplification, without limiting the invention or appended claims, certain practical embodiments of the present invention wherein:

FIG. 9 is a top or plan view of a bed utilized as part of a second jig for the bone cutting jig system of the present invention which is utilized to further dimension and contour bone segments previously formed on the first jig illustrated in FIGS. 1 through 5;

FIG. 10 is a top or plan view of a first embodiment of a cover plate which may positioned over the second jig bed shown in FIG. 9 for making certain prescribed cuts on or in bone segments cut on the first jig illustrated in FIGS. 1 through 5;

FIG. 11 is a right end exploded side view in elevation illustrating the combination of the cover plate of FIG. 10 used in combination with the second jig bed of FIG. 9;

FIG. 12 is a view in side elevation of an oscillating saw blade modified to be utilized in the second jig structure illustrated in FIGS. 9, 10 and 11;

FIG. 13 is a view in front elevation illustrating saw cut modifications administered to the implant of FIG. 6 with the apparatus of FIG. 11 in order to provide an ALIF implant;

FIG. 14 is a top or plan view of the bone implant segment shown in FIG. 13;

DETAILED DESCRIPTION OF THE PREFERRED EMBODIMENTS

Figure 1:
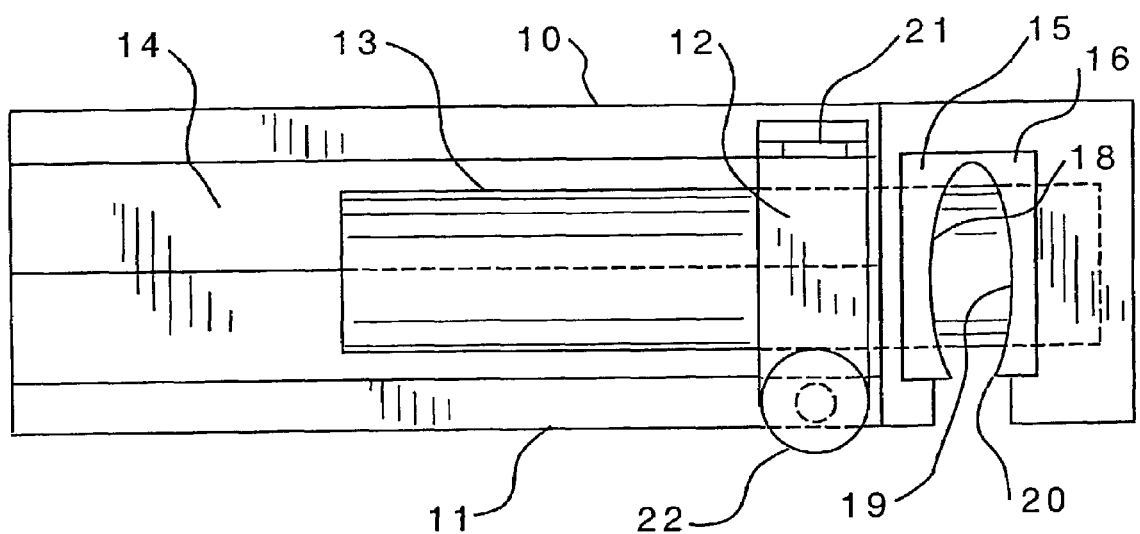
FIG. 1 is a top or plan view of a simplified embodiment of the first jig for one embodiment of the bone cutting jig system of the present invention.
Figure 2:
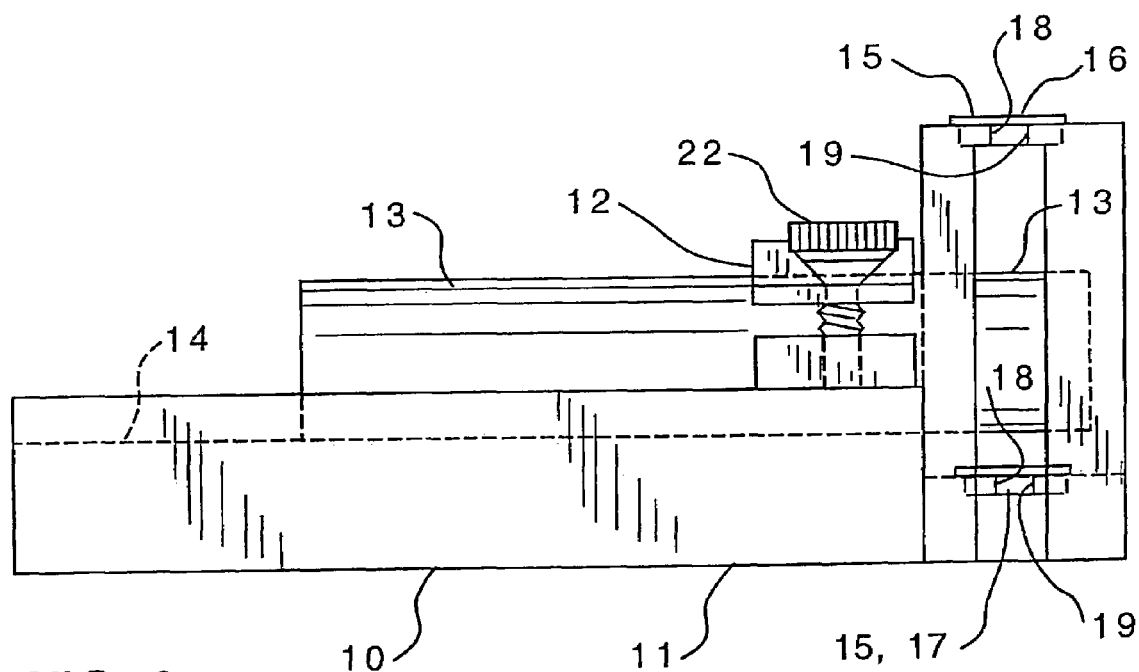
FIG. 2 is a view in front elevation of the first jig illustrated in FIG. 1.
Figure 3:
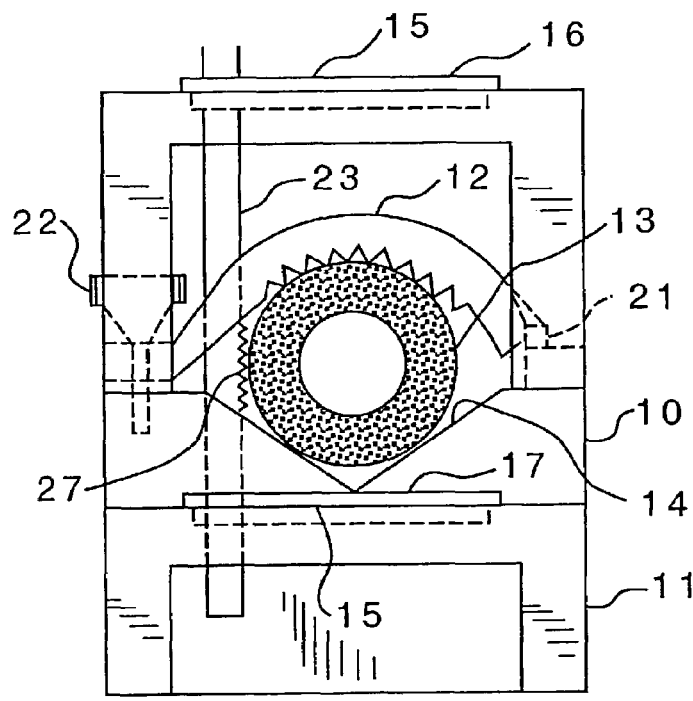
FIG. 3 is a right end view in side elevation of the apparatus shown in FIGS. 1 and 2.

In a first embodiment of the present invention pertaining to lumbar spinal implants, the cutting jig system of the present invention is comprised of three separate or distinct cutting jigs wherein the first cutting jig is a primary cutting jig which will normally be utilized first for forming an implant, and the second and third jigs may be incorporated or used as required or desired after the initial implant is formed on the first cutting jig. The first cutting jig 10 of the system is illustrated in FIGS. 1, 2 and 3. The first jig 10 is provided with a bed 111 having a clamp 12 for clamping the femur shaft donor bone 13, which is positioned in the V-trough 14 of bed 11, for cutting. Clamp 12 is a simple bar clamp mechanism which is hinged at 21 and is adjustably clamped downward against donor bone 13 by means of clamp thumb screw 22.

A removable cutting guide insert 15 is provided in the form of upper and lower insert pair 15 comprised of respective upper insert 16 and lower insert 17. Each insert is received in fixed orientation on bed 111 as illustrated and is provided with two spaced cutting blade cutting guides 18 and 19 which are configured for transversely cutting out a segment of the donor bone 13 clamped on bed 11 to a predetermined shape and dimension in order to provide a custom fit lumbar interbody fusion implant. The spaced cutting blade cutting guides 18 and 19 are open-ended as indicated at 20 and dimension and to receive and guide there against a reciprocating saw blade 23 as illustrated in FIG. 3, or a router blade (not shown), for cross cutting through the donor bone 13 along the predetermined profile provided by the guides 18 and 19.

Figure 6:
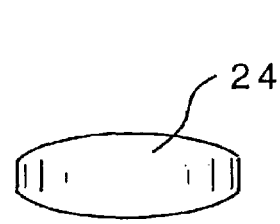
FIG. 6 illustrates in a side elevation an example of a PLIF implant cut from femur donor bone on the first jig illustrated in FIGS. 1, 2 and 3.
Figure 7:
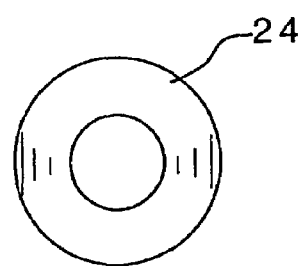
FIG. 7 is a top or plan view of the implant shown in FIG. 6.

It will be noted that the spaced cutting guides 18 and 19 are configured for cutting a bi-convex or lens shaped cross sectional segment from the donor bone as is illustrated in FIGS. 6 and 7. This PLIF insert 24 has an overall 11° taper which enhances the implants capability to impart a lordosis to the fused lumbar segment. Typically this PLIF insert may be designed to be 22 mm long and the length, as will be seen hereinafter, may be made shorter or longer according to the wishes of the surgeon. This femoral shaft segment or insert 24 which has been cut on the main or first jig 10 with a reciprocating saw or router provides a resultant femoral ring as is illustrated in FIG. 7 with the bi-convex configuration illustrated in FIG. 6.

The use of a matching upper and lower insert pair 15 in the form of inserts 16 and 17 is preferred in order to respectively guide upper and lower portions of the reciprocating saw blade or router blade as it is pressed along the cutting guide surfaces 18 and 19 respectively. Multiple cutting guide insert pairs 15 are provided and each set is provided with a different matching cutting guide profile from another insert set so that the surgeon has many choices in dimension and shape for custom cutting the donor bone implant segments In other words, each upper and lower insert pair 15 has a different saw guide profile from another pair for providing multiple choices in dimension and shape for custom cut donor bone implant segments 24.

Figure 4:
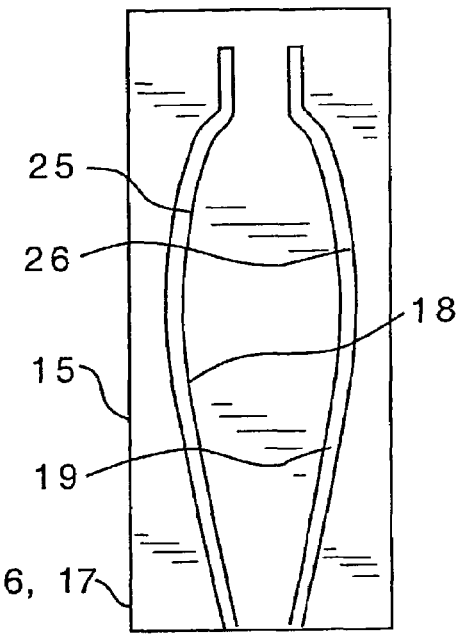
FIG. 4 is an enlarged plan view illustrating a second embodiment of the removable cutting blade cutting guide utilized in the apparatus shown in FIGS. 1, 2 and 3.
Figure 8:
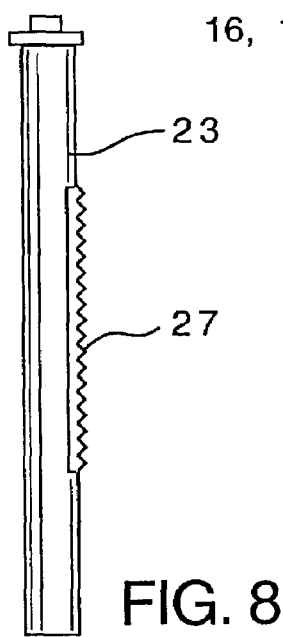
FIG. 8 is a view in side elevation illustrating a reciprocating saw blade modified for use with a reciprocating saw on the apparatus shown in FIGS. 1 through 5 for cutting bone implant segments as illustrated in FIGS. 6 and 7.
Figure 5:
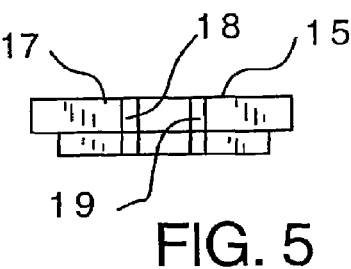
FIG. 5 is a bottom end view in elevation of the structure shown in FIG. 4.

The cutting guides 18 and 19 illustrated in the structure of FIGS. 1, 2 and 3 are open whereby the surgeon in order to guide the reciprocating saw or router blade must press the saw blade against the profiles of the cutting guides 18 and 19. It is therefore preferable to substitute these inserts rather with cutting guides 18 and 19 as shown in FIGS. 4 and 5 which are comprised of open-ended slots 25 and 26 which correspondingly provide and confine the profiles of cutting guides 18 and 19. The reciprocating saw blade 23 is illustrated in detail in FIG. 8 and it differs from ordinary present day reciprocating saw blades wherein the saw teeth 27 provided on the front edge of the blade are only provided in the mid portion and the upper and lower portions beyond the teeth 27 are smooth so that the teeth do not engage and mar the profiles of the cutting guides 18 and 19. A similar design may be provided for a router blade.

Once the femoral shaft has been cut on the first jig 10 with a reciprocating saw or router, the resultant bi-convex femoral ring 24 is placed into the cutting bay of the second cutting jig 30 of the present invention as shown in FIGS. 9, 10 and 11 for additional precision cuts. This second jig 30 is provided with a bed 31 having a trough 32 therein which is contoured and dimensioned to receive and seat bottom portions of an implant, such as the implant 24, cut from donor bone on the first jig. This second jig includes also one of several choices of cover plates 33 which are dimensioned and contoured on their bottom face as indicated at 34 to engage upper portions of the implant. The particular cover plate illustrated in FIGS. 10 and 11 is designated as a first cover plate 35. Other possible cover plates to be used in combination with the bed 31 will be illustrated hereinafter.

In the structure of FIGS. 9, 10 and 11, a clamp mechanism 36 is employed for drawing the cover plate 35 to the bed 31 in alignment for clamping an implant therebetween. This mechanism includes four vertical pegs or posts 37 which are positioned at the four corners of the bed 31. These posts protrude through the corresponding guide openings 38 in cover plate 35. When pressing cover plate 35 downwardly over top of bed 31, spring loaded lock slides 39 are displaced or slid to the right as viewed in FIG. 10 due to the protrusion of posts 37 through corresponding openings 38. Lock edges 40 of lock slides 39 engage against the vertical row of locking teeth 41 provided on the vertical posts 37 to thereby lock the cover plate 35 downwardly on to bed 31 in perfect alignment.

Parallel cutting blade guide slots 42 are provided in the cover plate 35 for guiding a cutting blade to correspondingly cut an implant positioned under the cover plate and received in the trough 32 of bed 31 for cutting corresponding slots in implant 24 as indicated at 43 to provide ridges 44 as illustrated in FIGS. 13 and 14. This resultant insert or implant 24 provides an ALIF (anterior lumbar inter-body fusion) ring, complete with lordotic curve to aid in precise fit and the ridges help to avoid post surgical back out of the implant.

The oscillating saw blade 45 as illustrated in FIG. 12 has been designed by the inventor to assist in precisely cutting the slots 43. The oscillating blade 45 is provided with teeth 46 at the bottom thereof and is also provided with lateral extending pegs 47 to limit the depth of penetration of the blade down into the slots 42 provided in cover plate 35. A router blade may be similarly configured to obtain the same results.

Figure 15:
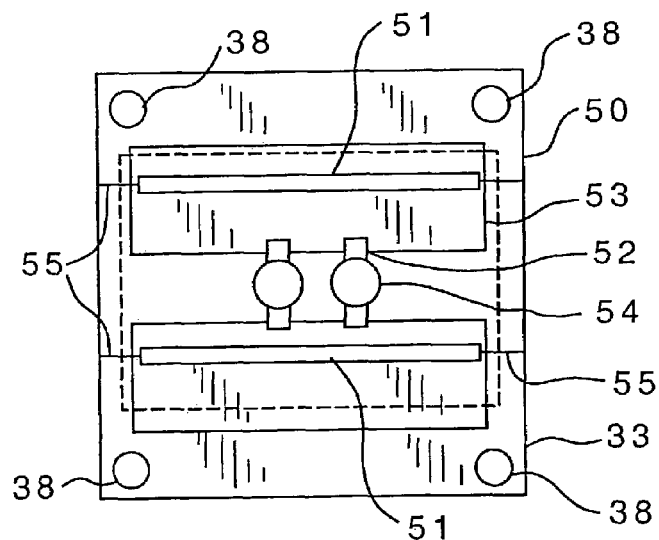
FIG. 15 is a plan view illustrating a second embodiment of a cover plate to be utilized in combination with the second jig bed structure shown in FIG. 9 in order to provide different cuts to an implant previously formed on the first jig illustrated in FIGS. 1 through 5.
Figure 16:
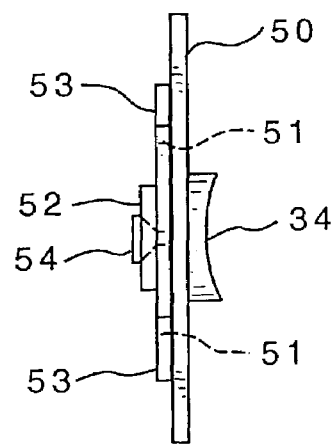
FIG. 16 is a right end view in side elevation of the cover plate structure shown in FIG. 15.

Turning next to FIGS. 5, 15 and 16, a second cover plate 50 is illustrated for use on second jig bed 31 of FIG. 9. Similar elements are designated with the same reference numerals. This cover plate 50 is designed to include a mechanism for adjusting spacing between the slots 51. Here clamp bars 52 adjustably clamp slidable plates 53 with clamp thumb screws 54. This permits adjustment of spacing between the slots 51.

Figure 17:
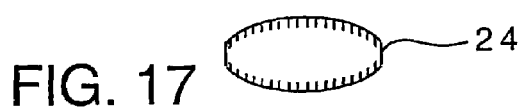
FIG. 17 illustrates a view in front elevation of an implant segment previously formed and as modified with the structure of FIGS. 15 and 16.
Figure 18:
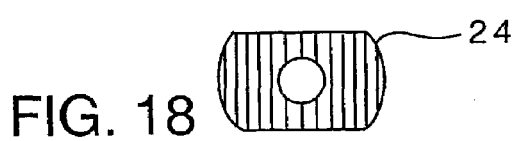
FIG. 18 is a top or plan view illustrating the modified implant segment shown in FIG. 17.

Witness lines or reference lines 55 are provided both on cover plate 50 and second jig bed 31 as illustrated in FIG. 9. These reference lines are suggested guide lines for optimal profile for typical 22 mm spacing. This spacing provides a cut on the femoral implant 24 as shown in FIGS. 17 and 18, as best illustrated in the top view of FIG. 18. The cover plate 50 of FIG. 15 may be utilized also to sever the ring implant shown in FIG. 14 horizontally in half to thereby provide a TLIF (Transforamenal or lateral lumbar inter-body fusion implant).

Figure 19:
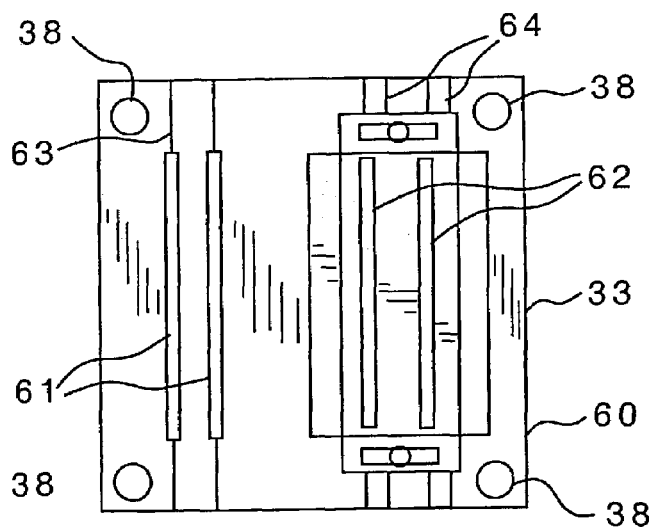
FIG. 19 is a plan or top view of a third embodiment of a cover plate to be utilized in combination with the second jig bed shown in FIG. 9 in order to form yet different cuts on an implant previously formed on the first jig illustrated in FIGS. 1 through 5.
Figure 20:
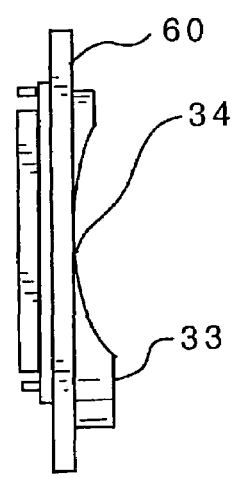
FIG. 20 is a right end view in side elevation of the cover plate shown in FIG. 19.

Yet another or third variation in the cover plate 33 is illustrated in FIGS. 19 and 20 as cover plate 60. In this cover plate 60, there are fixed slots 61 on the left side and movable spaced slots 62 on the right side. Also, reference lines 63 are provided on the left side of the cover plate 60 for suggested optimal spacing. Similarly on the right hand side of cover plate 60, reference lines 64 are also provided to suggest optimal positioning of the slots 62. The same alignment slots are also provided on the bed 31 of the second jig as shown in FIG. 9.

Figure 21:
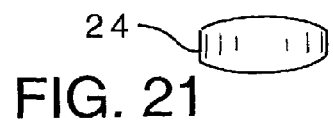
FIG. 21 is a view in front elevation illustrating a bone implant previously cut on the first jig represented in FIGS. 1 through 5 and as modified by cuts applied thereto through the use of the cover plate shown in FIGS. 19 and 20.
Figure 22:
FIG. 22 is a left end view in elevation of the bone segment shown in FIG. 21.
Figure 23:
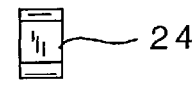
FIG. 23 is a right end view in elevation of the bone segment shown in FIG. 21.
Figure 24:
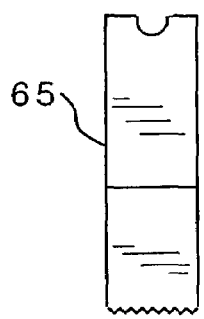
FIG. 24 illustrates in side elevation a modified oscillating blade for use in combination with the cover plate structure of FIGS. 19 and 20.
Figure 25:
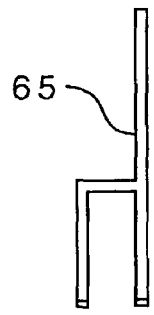
FIG. 25 is a right side view in elevation of the saw blade structure illustrated in FIG. 24.

Slots 61 and 62 are typically spaced 8 mm apart. Slots 62 may be positioned to the left or to the right to allow for optimal placement of the cuts, again based on the surgeon's preference. This lab cut is made with a double oscillating blade 65 as illustrated in FIGS. 24 and 25 or an appropriate router blade and provides the side cuts for implant 24 shown in FIG. 21 as is best illustrated by the two end views of FIGS. 22 and 23.

The system is extremely versatile. For example, cover plate 50 of FIG. 15 may be utilized to form a TLIF implant, and the cover plate 60 of FIG. 20 may be used to form a custom PLIF implant.

The clamping mechanism 39 shown for the cover plate 35 in FIG. 10 is eliminated from the cover plate structures shown in FIGS. 15, 16, 19 and 20 for the sake of clarity.

Figure 26:
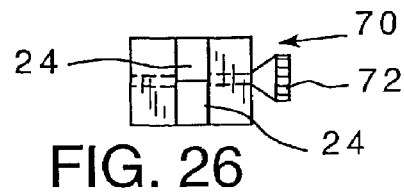
FIG. 26 is a top or plan view of a retaining mechanism which represents a third cutting jig for the bone cutting jig system of the present invention for retaining a donor bone implant as a base for a drill guide.
Figure 27:
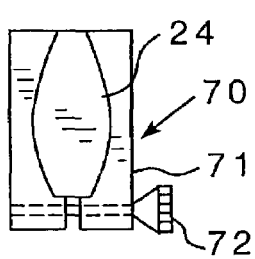
FIG. 27 is a view in front elevation of the apparatus shown in FIG. 26.
Figure 28:
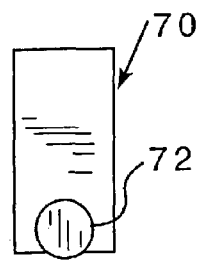
FIG. 28 is a view in right side elevation of the structure shown in FIG. 27.
Figure 29:
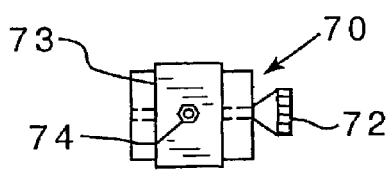
FIG. 29 is a top or plan view of the clamp structure shown in FIG. 26 with a drill guide applied thereto for cutting a notch along one side of an implant maintained in the retaining mechanism with a drill.
Figure 30:
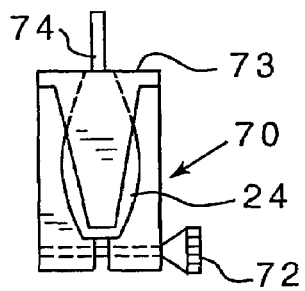
FIG. 30 is a view in front elevation of the combination structure illustrated in FIG. 29.
Figure 31:
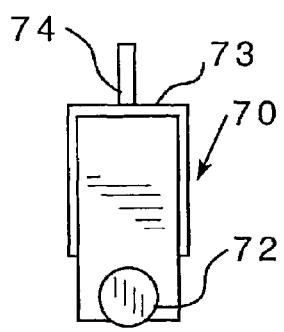
FIG. 31 is a view in right side elevation of the combination structure shown in FIG. 30.

Turning next to the structure illustrated in FIGS. 26 through 31, a third cutting jig 70 is illustrated which retains an implant 24 cut from cadaver donor bone on the first jig 10. In actuality, a PLIF pair 24 is retained in the third jig 70. The basic portion of the clamp body 71 is illustrated in FIGS. 26, 27 and 28 and includes a thumb screw 72 for clamping the clamp body against the preformed implants 24 to retain them for drilling.

Basically the cover plate 35 of FIG. 10 is used to cut ridges or teeth in the implant, the cover plate 50 of FIG. 15 is used to cut the length of the implant and the cover plate 60 of FIG. 19 is used to cut the width of the implant. However, the use of these cover plates is not limited to these specific functions.

Figure 32:
FIG. 32 is a view in front elevation illustrating one implant which was formally retained in the structures illustrated in FIGS. 26 through 31 and which has been drilled in the jig to provide a retaining notch for engaging the implant with an implant instrument.
Figures 33, 34:
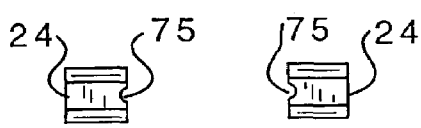
FIG. 33 is a view in left side elevation of the modified implant shown in FIG. 32.
FIG. 34 is a view in right side elevation of the modified bone implant structure of FIG. 32.
Figure 35:
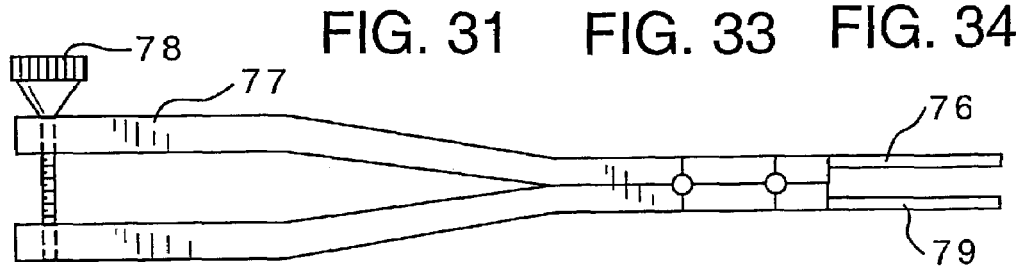
FIG. 35 is a view in side elevation of an implant insertion clamp of the present invention utilized to grasp and insert the bone implant structure illustrated in FIGS. 32, 33 and 34.
Figure 36:
FIG. 36 is a right end view in side elevation of the tool shown in FIG. 35 illustrating the end configuration of the finger jaws for the tool.

After clamping the implants 24 as shown in FIGS. 26, 27 and 28, a drilling guide 73 is slid or applied over top of the clamping body 71 and is provided with a drill guide tube 74. A drill of appropriate size is inserted downwardly into the drill guide tube 74 and drills out a corresponding hole between the two adjacent implants 24. The results are illustrated in FIGS. 32, 33 and 34. Here each one of the implants 24 is thus drilled to provide a notch 75 along the side thereof. This notch 75 is provided for mating engagement with a finger jaw 76 of the insertion clamp 77 shown in FIG. 35 for gripping and controlling the implant during lumbar insertion. The insertion clamp 77 is constructed of surgical steel and is provided with a thumb screw clamp mechanism 78 to adjustably spread or close jaws 76 and 79 to release or clamp an implant 24 therebetween.

The previous specifications pertain to the construction of spinal implants for the lumbar area. However, cervical and thoracic areas of the spine also call for the construction of spinal implants during surgery in accordance with the teachings of the present invention to aid in the stabilization and fusion of the involved spinal segments. As with lumbar implants, implants for these areas are also pre-machined and supplied by surgical supply vendors and they are quite expensive. The use of donor bone is desired in order to produce a biologically active implant for the purpose of inter-body support in the cervical and thoracic levels since the body will eventually assimilate the inter-body material and convert it into living bone.

As with the lumbar implant jig system of the present invention, implants for cervical and thoracic applications are formed in accordance with the teachings of the present invention from available stock of inexpensive frozen donor bone from a bone bank. In accordance with the following teachings a thoracic implant jig is provided to form the implant from femur bone and in cervical applications the donor bone utilized is fibula. Unlike the lumbar PLIF jig previously described, the cervical and thoracic jigs cut a single implant, since these areas of application do not require paired implants as does the lumbar area.

Figure 37:
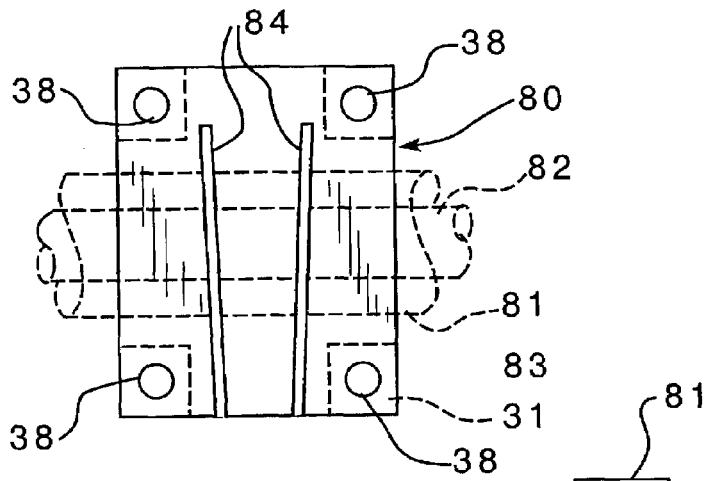
FIG. 37 is a plan view of a first cutting jig for making initial cuts to femur or fibula donor bone for cervical or thoracic implant applications.
Figure 38:
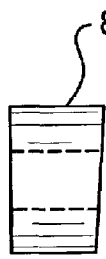
FIG. 38 is a plan view of a segment of femur donor bone cut on the first jig assembly illustrated in FIG. 37.
Figure 39:
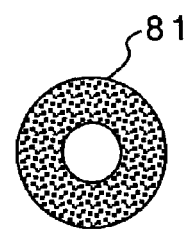
FIG. 39 is a right side or end view of the bone segment shown in FIG. 38.

Referring to FIG. 37, a first cutting jig 80 is illustrated and is adapted for making initial cuts of either femur or fibula donor bone for initial formation respectively of a cervical or thoracic implant. The outline of a femur bone segment is illustrated as being clamped into the jig at 81 and the outline of a fibula segment is illustrated at 82. The cutting jig 80 basically consists of an underlying jig bed 31 similar to that illustrated in FIG. 11 with a different cover plate 83 clamped thereon with the same mechanism as illustrated for the devices shown in FIGS. 10 and 11.

Instead of cutting a lens shape as is used in a PLIF insert, a three degree wedge is used and cut in the bone segment with the greatest height of the implant to be positioned anteriorly. The guide slots 84 diverge at three degrees and provide cutting blade guided access for either a router blade or a reciprocating saw blade. The bone inserts can be sized between 5 to 22 mm wide in 1 mm increments to allow maximum flexibility in the operating room.

Figure 41:
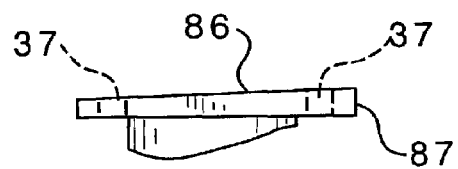
FIG. 41 is a view in front elevation of the base plate illustrated in FIG. 40.
Figure 42:
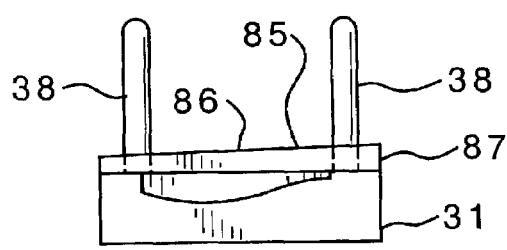
FIG. 42 is a view in side elevation illustrating the base plate of FIGS. 40 and 41 mounted on a cutting jig bed of the type initially illustrated in FIG. 11.

The base 31 for the cutting jig is the same base illustrated in FIG. 11. It is however modified for receiving and holding the donor bone segment initially cut on the first jig assembly shown in FIG. 80 by the application thereon of a base plate 85. The base plate 85 seats on the jig bed 31 as illustrated in FIG. 42 and provides an upper surface 86 which is roughened to grip the implant. In addition, the thickness of the plate portion 87 of base plate 85 provided with a varying thickness with a 1.5° slope from the anterior or low end to the posterior or high end when viewed from the side as seen in FIGS. 41 and 42. This slope is designed to accommodate the 3° of lordosis that was cut into the fibular ring initially on the jig illustrated in FIG. 37. Similarly a cover plate selected from the group of cover plates 90, 91 and 92 is applied over top of base plate 85 for guiding different desired cuts to the implant segment sandwiched between the cover plate 90, 91, or 92, and the bed plate 85.

Figure 40:
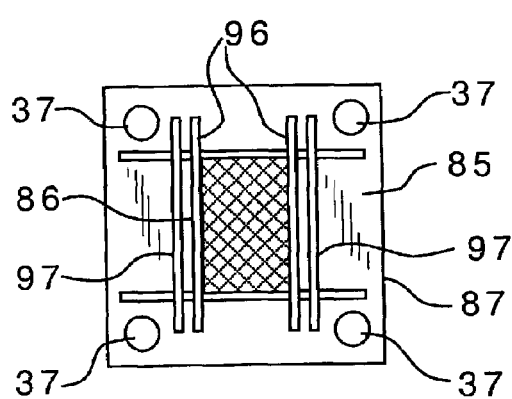
FIG. 40 is a plan view of a base plate to be secured to a jig bed of the type illustrated in FIG. 11 for making further dimensions and contours to an implant initially cut on the first jig system illustrated in FIG. 37.
Figure 43:
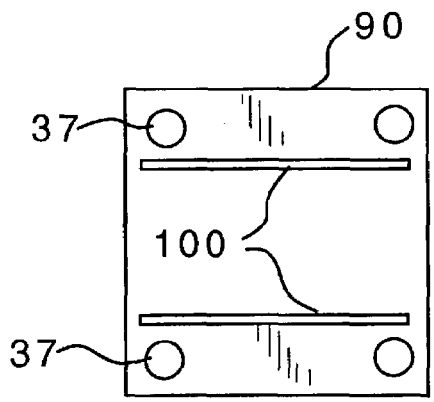
FIG. 43 is a plan view of a cover plate for use with the jig base assembly of FIG. 42 for making specific desired cuts to an implant.
Figure 47:
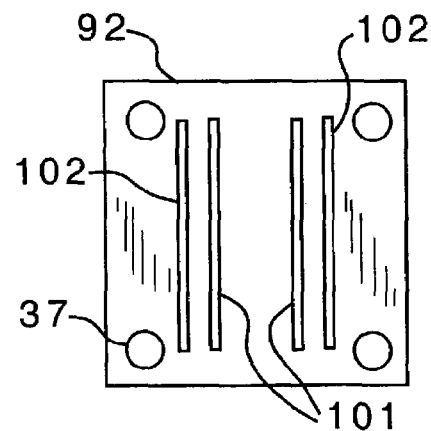
Figure 48:
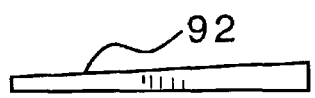

A cervical modification will be described first. A segment of fibula or a fibula strut is cut within the jig 80 with a three degree taper to a desired height. This wedge shaped fibula ring is then transferred to a second cutting jig bed illustrated in FIGS. 40, 41 and 42. The upper surface 86 of the bed plate 85 is applied with horizontal grooves 95 spaced at 11 mm, a vertical pair of grooves 96 spaced at 11 mm and an additional outside pair of vertical grooves 97 spaced at 14 mm. These grooves are aligned to accommodate cover plates 90 and 92 respectively of FIGS. 43 and 47 so that the cutting blade which is penetrating and guided by the slots 100 in cover plate 90, or the slots 101 or 102 of the cover plate shown in 92, will correspond respectively with the grooves underlying these slots in the bed plate 85. This permits insertion of a router cutting blade, a reciprocating saw blade or an oscillating saw blade to not only penetrate through the slots of cover plates 90 and 92, but also permits the cutting blade to penetrate completely through the bone retained in the jig so that cutting blade may penetrate on into underlying grooves 95, 96 and 97. In other words, these grooves 95, 96 and 97 provide relief or clearance for the saw blade or cutting blade.

The cover plates 90, 91 and 92 of FIGS. 43 through 48 are held in place by the same quick release latching mechanism described for the cover plates as illustrated in FIGS. 10 and 11. Each of the cover plates 90, 91 and 92 are also constructed whereby they have a 1.5° slope so that when combined with the wedge shape of the cutting bed 85, when clamping the implant therebetween, allows for the 3° of lordosis of the graft to be accommodated therebetween. As with the top 86 of the base plate 85, the under surfaces of the cover plates 90, 91 and 92 are also roughened, such as with a file surface, to prevent slipping of bone segment clamped between the cover plates and the bed plate 85.

Figure 45:
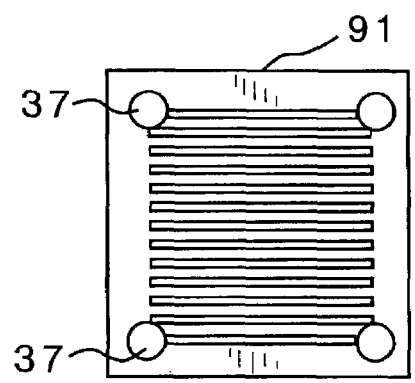
FIGS. 45, 46, 47 and 48 illustrate respectively plan and front edge views of two more cover plate alternatives having different cutting guide slots therein for making more cuts and contours to an implant for ultimate use in cervical or thoracic applications.
Figure 44:
FIG. 44 is an edge view in front elevation of the cover plate illustrated in FIG. 43.
Figure 46:
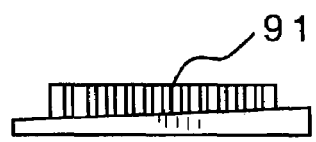

Cover plate 90 permits cutting of the implant to the appropriate width for a cervical implant, and the horizontal cutting guide slots 100 permit the implant to be cut to the appropriate height. The cover plate 91 illustrated in FIGS. 45 and 46 is utilized to provide grooves into the graft or implant as was done also in the application of lumbar implants.

When cutting a thoracic implant, the same jigs and cover plates are utilized and the initial femur segment 81 is cut in the initial jig 80 (FIG. 37) to the appropriate wedge shape as previously discussed with regard to the initial cut of the fibula ring segment for a cervical modification. In the same manner the cut femur ring is transferred to the base plate 85 illustrated in FIG. 42 for additional cutting.

However, unlike the cervical implant, the only other modification necessary for the thoracic implant is the placement of horizontal grooves on the two ends or faces of the graft. Accordingly, only cover plate 91 of FIGS. 45 and 46 is required for cutting the grooves.

Once all the cuts are made, the product is a ring of bone, the depth and width of which equals to the size of the femur cross section (anterior-posterior), and 5 to 22 mm in height. There is also a 3° kyphosis to this thoracic implant. The central marrow cavity of the former femur can be packed with the patient's own bone or with a bone substitute or stimulator, such as bone morphogenic protein. This provides for rapid fusion and eventually the femur implant will be replaced by living bone.

I claim:

1. A cutting jig system serving as a guide for cutting spinal spacer implants from donor bone for spinal fusions, the system comprising:
   a first jig having a bed with clamp means for clamping donor bone positioned on said bed for cutting;
   a removable cutting guide insert received in fixed orientation on said bed and having two spaced cutting blade cutting guides configured for transversely cutting out a segment of donor bone clamped on said bed to a predetermined shape and dimension to provide a custom fit lumbar inter-body fusion implant;
   said cutting guide insert comprised of a spaced upper and lower pair of inserts having identical cutting blade guide profiles therein which are open to one side of said jig for receiving and guiding respectively upper and lower portions of a cutting blade from said one side;
   said jig open at said one side and thereby forming a cavity therein for exposing bone clamped in said first jig to be cut and receiving a cutting blade through said side opening, and said spaced cutting blade cutting guides of both said upper and lower inserts being open ended at said one side of said jig and dimensioned to thereby simultaneously receive and guide upper and lower portions respectively of a vertically reciprocated cutting blade into said cavity from said one side of said jig for cutting through donor bone clamped on said bed along a predetermined profile.

2. The cutting jig system of claim 1, wherein said spaced cutting blade cutting guides are configured for cutting a bi-convex cross sectional segment from the donor bone.

3. The cutting jig system of claim 1, including multiple of said cutting guide inserts, each insert having different cutting guide profiles from another insert for providing multiple choices in dimension and shape for custom cut donor bone implant segments.

4. The cutting jig system of claim 1, wherein said bed includes a trough for receiving an elongate donor bone segment therein for clamping.

5. The cutting jig system of claim 1, including: a second jig having a bed with a trough therein which is contoured and dimensioned to receive and seat bottom portions of an implant cut out from donor bone on said first jig, a cover plate dimensioned and contoured to engage upper portions of said implant and having a clamp mechanism for drawing said cover plate to said bed for said second jig in parallel alignment to said bed for clamping said implant therebetween, and cutting blade guide slots in said cover plate for guiding a cutting blade to correspondingly cut said implant.

6. The cutting jig system of claim 5 including cutting profile reference line indicia on the bed for said second jig for providing suggested cutting profiles and proper alignment of said cover plate.

7. The cutting jig system of claim 1, including means for retaining an implant cut out from donor bone on said first jig and having a drill guide for guiding a drill to cut a notch along one side of said implant for mating engagement with a finger jaw on an insertion clamp for gripping and controlling the implant during lumbar insertion.

8. The cutting jig system of 7, including an insertion clamp having a pair of parallel finger jaws for releaseably clamping opposite sides of said implant with one of said finger jaws seated in said notch.

* * * * *